(12) United States Patent
Baril et al.

(10) Patent No.: US 11,850,106 B2
(45) Date of Patent: Dec. 26, 2023

(54) CLEANING CAP FOR A SURGICAL ACCESS DEVICE

(71) Applicant: Covidien LP, Mansfield, MA (US)

(72) Inventors: Jacob C. Baril, Norwalk, CT (US); Matthew A. Dinino, Newington, CT (US); Saumya Banerjee, Hamden, CT (US); Justin Thomas, New Haven, CT (US); Garrett P. Ebersole, Hamden, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 450 days.

(21) Appl. No.: 16/868,213

(22) Filed: May 6, 2020

(65) Prior Publication Data
US 2021/0346122 A1    Nov. 11, 2021

(51) Int. Cl.
*A61B 90/70*    (2016.01)
*A61B 17/34*    (2006.01)

(52) U.S. Cl.
CPC .......... *A61B 90/70* (2016.02); *A61B 17/3423* (2013.01); *A61B 17/3498* (2013.01); *A61B 2090/701* (2016.02)

(58) Field of Classification Search
CPC .............. A61B 2090/701; A61B 90/70; A61B 17/3423; A61B 17/3498
See application file for complete search history.

(56) References Cited

U.S. PATENT DOCUMENTS

| | | |
|---|---|---|
| 946,370 A | 1/1910 | Kelmel |
| 2,850,754 A | 9/1958 | Davis |
| 3,308,825 A | 3/1967 | Cruse |
| 4,281,646 A | 8/1981 | Kinoshita |
| 4,543,683 A | 10/1985 | Goldman |
| 4,643,726 A | 2/1987 | Gegelys |
| 4,887,508 A * | 12/1989 | Bianco ............... A46B 7/04 15/104.11 |
| 4,919,113 A | 4/1990 | Sakamoto et al. |
| 4,941,872 A | 7/1990 | Felix et al. |
| 5,077,861 A | 1/1992 | Bokat |
| 5,207,213 A | 5/1993 | Auhll et al. |
| 5,274,874 A | 1/1994 | Cercone et al. |

(Continued)

FOREIGN PATENT DOCUMENTS

| | | |
|---|---|---|
| CN | 108451608 A | 8/2018 |
| DE | 102008059633 A1 | 6/2010 |

(Continued)

OTHER PUBLICATIONS

Extended European Search Report dated Oct. 1, 2021 issued in corresponding EP Appln. No. 21172391.0.

*Primary Examiner* — Brian D Keller
*Assistant Examiner* — Robert C Moore
(74) *Attorney, Agent, or Firm* — Carter, DeLuca & Farrell LLP

(57) ABSTRACT

A surgical access assembly includes a surgical access device and a cleaning cap. The surgical access device includes an elongated shaft defining an access lumen therethrough and having a distal portion terminating at a distal tip. The cleaning cap is disposed over the distal portion of the elongated shaft. The cleaning cap includes an instrument channel aligned with the access lumen and wipers disposed within the instrument channel.

20 Claims, 6 Drawing Sheets

(56) References Cited

U.S. PATENT DOCUMENTS

| | | | |
|---|---|---|---|
| 5,313,934 A | 5/1994 | Wiita et al. | |
| 5,337,730 A | 8/1994 | Maguire | |
| 5,339,800 A * | 8/1994 | Wiita | A61B 90/70 |
| | | | 600/109 |
| 5,382,297 A | 1/1995 | Valentine et al. | |
| 5,392,766 A | 2/1995 | Masterson et al. | |
| 5,400,767 A | 3/1995 | Murdoch | |
| 5,456,681 A * | 10/1995 | Hajjar | A61B 18/24 |
| | | | 606/15 |
| 5,514,084 A | 5/1996 | Fisher | |
| 5,518,502 A | 5/1996 | Kaplan et al. | |
| 5,630,795 A | 5/1997 | Kuramoto et al. | |
| 5,735,792 A | 4/1998 | Vanden Hoek et al. | |
| 5,842,971 A | 12/1998 | Yoon | |
| 5,931,833 A | 8/1999 | Silverstein | |
| 5,944,654 A | 8/1999 | Crawford | |
| 6,086,275 A * | 7/2000 | King | A46B 11/0041 |
| | | | 15/160 |
| 6,293,907 B1 | 9/2001 | Axon et al. | |
| 6,354,992 B1 | 3/2002 | Kato | |
| 6,387,044 B1 | 5/2002 | Tachibana et al. | |
| 6,447,444 B1 | 9/2002 | Avni et al. | |
| 6,682,165 B2 | 1/2004 | Yearout | |
| 6,755,782 B2 | 6/2004 | Ogawa | |
| 6,923,759 B2 | 8/2005 | Kasahara et al. | |
| 7,097,629 B2 | 8/2006 | Blair | |
| 7,300,445 B2 | 11/2007 | Adams | |
| 7,316,683 B2 | 1/2008 | Kasahara et al. | |
| 7,339,341 B2 | 3/2008 | Oleynikov et al. | |
| 7,361,166 B2 | 4/2008 | Bosse et al. | |
| 7,530,984 B2 | 5/2009 | Sonnenschein et al. | |
| 7,596,828 B2 | 10/2009 | Evdokimo | |
| 7,762,959 B2 | 7/2010 | Bilsbury | |
| 7,922,701 B2 | 4/2011 | Buchman | |
| 7,959,561 B2 | 6/2011 | Akui et al. | |
| 8,550,988 B2 | 10/2013 | Pribanic | |
| 9,763,567 B2 | 9/2017 | O'Prey et al. | |
| 2002/0022762 A1 | 2/2002 | Beane et al. | |
| 2002/0065450 A1 | 5/2002 | Ogawa | |
| 2003/0073955 A1 | 4/2003 | Otawara | |
| 2003/0199768 A1 | 10/2003 | Cespedes et al. | |
| 2004/0031119 A1 | 2/2004 | McKay | |
| 2005/0049460 A1 | 3/2005 | Mikkaichi et al. | |
| 2005/0197595 A1 | 9/2005 | Huang et al. | |
| 2005/0256373 A1 | 11/2005 | Bar-Or et al. | |
| 2006/0036277 A1 | 2/2006 | Kieturakis et al. | |
| 2006/0199998 A1 | 9/2006 | Akui et al. | |
| 2006/0258909 A1 | 11/2006 | Saadat et al. | |
| 2006/0293559 A1 * | 12/2006 | Grice, III | A61B 1/122 |
| | | | 600/102 |
| 2007/0032831 A1 | 2/2007 | Eigler et al. | |
| 2007/0149850 A1 | 6/2007 | Spivey et al. | |
| 2007/0208220 A1 | 9/2007 | Carter | |
| 2007/0208221 A1 | 9/2007 | Kennedy et al. | |
| 2007/0213667 A1 | 9/2007 | Prusmack | |
| 2007/0282253 A1 | 12/2007 | Sasaki | |
| 2007/0282356 A1 | 12/2007 | Sonnenschein et al. | |
| 2007/0299310 A1 | 12/2007 | Phillips | |
| 2008/0015618 A1 | 1/2008 | Sonnenschein et al. | |
| 2008/0188715 A1 | 8/2008 | Fujimoto | |
| 2008/0199356 A1 * | 8/2008 | Suter | A61B 90/70 |
| | | | 433/82 |
| 2008/0319266 A1 | 12/2008 | Poll et al. | |
| 2009/0049627 A1 | 2/2009 | Kritzler | |
| 2009/0105543 A1 | 4/2009 | Miller et al. | |
| 2009/0112065 A1 | 4/2009 | Harrel | |
| 2009/0240111 A1 | 9/2009 | Kessler et al. | |
| 2009/0270686 A1 | 10/2009 | Duke et al. | |
| 2009/0287052 A1 | 11/2009 | Amos et al. | |
| 2010/0030031 A1 | 2/2010 | Goldfarb et al. | |
| 2010/0174144 A1 | 7/2010 | Hsu et al. | |
| 2010/0225753 A1 | 9/2010 | Karasawa et al. | |
| 2011/0230716 A1 | 9/2011 | Fujimoto | |
| 2012/0238816 A1 * | 9/2012 | Gunday | A61B 1/00135 |
| | | | 600/114 |
| 2018/0344427 A1 * | 12/2018 | Rosenbaum | A61B 90/70 |
| 2021/0338272 A1 * | 11/2021 | Muthuchidambaram | |
| | | | A61B 17/3423 |

FOREIGN PATENT DOCUMENTS

| | | |
|---|---|---|
| EP | 1210904 A2 | 6/2002 |
| EP | 1323373 A2 | 7/2003 |
| EP | 1911409 A1 | 4/2008 |
| JP | 2005040184 A | 2/2005 |
| JP | 2005052229 A | 3/2005 |
| JP | 2007105314 A | 4/2007 |
| JP | 2007130167 A | 5/2007 |
| JP | 2008132282 A | 6/2008 |
| JP | 2008279202 A | 11/2008 |
| JP | 2010022758 A | 2/2010 |
| WO | 9824359 A1 | 6/1998 |
| WO | 2008153841 A2 | 12/2008 |
| WO | WO-2008153841 A2 * | 12/2008 ......... A61B 1/00087 |
| WO | 2019226855 A1 | 11/2019 |

* cited by examiner

CLEANING CAP FOR A SURGICAL ACCESS DEVICE

FIELD

The present disclosure relates generally to surgical devices. In particular, the present disclosure relates to a cleaning cap for a surgical access device for cleaning a surgical instrument positioned through the surgical access device.

BACKGROUND

Some surgical procedures, namely laparoscopy, hysteroscopy, and endoscopy, require the insertion of a visualization device into a body cavity. During such procedures, surgeons use visualization devices, such as laparoscopes, arthroscopes, and endoscopes, to observe features and structures within the body cavity. The view provided by these visualization devices may facilitate detection of physiological anomalies within the human body.

Visualization devices typically include a rigid or flexible rod. These rods generally contain light conductive fibers and lenses. An external light source usually provides illumination and is ordinarily connected to a proximal end of the rod. The fibers transmit light to the distal end of the visualization device through the rod. After providing adequate illumination, surgeons can inspect the internal structure of a body cavity by observing through an eyepiece, which is ordinarily located at the proximal end of the rod. Alternatively, visualization devices include cameras disposed at their distal end. These cameras transmit video signals to a monitor electrically linked to the rod of the visualization device. Visualization devices with cameras allow surgeons to perform surgical procedures while watching a monitor. Surgeons, however, must follow certain steps before they can properly use a visualization device.

Before introducing a visualization device into a body cavity, the body cavity is usually insufflated with gas or liquid. Thereafter, a surgical access device (e.g., a sleeve, a sheath, or other access port) is inserted through the wall of the body cavity. These surgical access devices ordinarily include a seal that prevents leakage of gas or liquid from within the body cavity. After the body cavity is properly insufflated, the visualization device is inserted through the surgical access device. Surgeons can then view the inner features of the body cavity through the visualization device disposed within the surgical access device.

Surgical access devices are not necessarily operatively coupled to a specific visualization device. One surgical access device is often used with multiple visualization devices and/or other surgical instruments. To use a different visualization device, a surgeon can simply retract a visualization device positioned within the surgical access device and insert another visualization device through the same surgical access device. Alternatively, the surgical access device may have multiple ports.

While extracting and inserting a visualization device, bodily fluids and debris can enter the inner portions of the surgical access device. These fluids and debris may stick to the surfaces of the newly inserted visualization device and soil the lens thus reducing visibility through the lens. Additionally, lens smudging, soiling, and/or other visual obstructions, such as fogging, can occur during use and manipulation of the visualization device within the body cavity that obscures the surgeon's view.

The most common approach to dealing with obscured lenses has been to completely remove the visualization device from the surgical access device and to manually clean it. While effective, the need to withdraw the visualization device from the surgical access device, clean it, reinsert it, and relocate the target, is inefficient and can lead to surgical delay or occur at inopportune times when visualization can impact the procedural outcome. Others have proposed to incorporate a spray wash nozzle on the visualization device itself or on the surgical access device to permit cleaning of the lens without removing the visualization device from the patient. These devices, however, may be relatively expensive and require the provision of irrigation passages and cleaning fluids.

SUMMARY

This disclosure generally relates to a cleaning cap for a surgical access device for cleaning a visualization device, or other surgical instrument, while the surgical instrument remains inserted through the surgical access device. The cleaning cap is configured to clean a distal end portion of the surgical instrument extending through the surgical access device. The cleaning cap is quickly and easily coupled to a distal end portion of the surgical access device to reduce soiling on the surgical instrument inserted through the surgical access device.

In some aspects, the cleaning cap is configured to be installed on pre-existing surgical access devices. For example, the cleaning cap may be universal and fit standard sized trocars, cannulas, and/or sleeves (e.g., 5-15 mm surgical access devices).

In some aspects, the cleaning cap is formed from a flexible material, such as a soft rubber, and has an inner geometry utilized to clean the distal end portion of a surgical instrument passed therethrough. Cleaning is performed by retracting and advancing the surgical instrument through the cleaning cap, removing soiled material from the distal end portion of the surgical instrument that can impair the function of the surgical instrument (e.g., obstruct visualization through a lens of a visualization device). As compared to traditional methods in which the surgical instrument is removed from the surgical access device and cleaned, e.g., with a gauze pad, the cleaning cap provides a quick and simplified method of cleaning and can reduce downtime in the operating room.

In one aspect, the disclosure provides a surgical access assembly including a surgical access device and a cleaning cap. The surgical access device includes an elongated shaft defining an access lumen therethrough, and has a distal portion terminating at a distal tip. The cleaning cap is disposed over the distal portion of the elongated shaft. The cleaning cap includes an instrument channel aligned with the access lumen and includes wipers disposed within the instrument channel.

The distal portion of the surgical access device may be disposed within an annular pocket of the cleaning cap. The annular pocket may be defined between inner and outer annular walls of the cleaning cap. The instrument channel may be defined by an inner surface of the inner annular wall and may be disposed within the access lumen of the surgical access device. The wipers may extend from the inner surface of the inner annular wall radially into the instrument channel.

The cleaning cap may mimic the shape of the distal portion of the surgical access device.

The wipers may be formed from a flexible material and, in some aspects, may be formed from rubber. The cleaning cap may be monolithically formed from the flexible material.

Each of the wipers may include a full disc-shaped body defining an opening therethrough that has a smaller diameter than that of the instrument channel. The wipers may be disposed in longitudinally spaced relation relative to each other. The openings of the wipers may vary in size and may be concentric with each other.

Each of the wipers may include a partial disc-shaped body. A first set of the wipers may extend from a first side of the inner surface of the inner annular wall radially into the instrument channel and a second set of the wipers may extend from a second side of the inner surface of the inner annular wall radially into the instrument channel. The first and second sets of the wipers may be disposed in opposed relation relative to each other and may be longitudinally offset with respect to each other to define a tortuous path through the instrument channel.

The surgical access assembly may further include a surgical instrument including an elongated tubular body having a distal end portion terminating at a tip portion. The surgical instrument may be positionable through the surgical access device and the cleaning cap. The surgical instrument may be a visualization device including a lens disposed at the tip portion. The distal end portion of the surgical instrument may be movable through the cleaning cap in proximal and distal directions. Movement of the surgical instrument within the cleaning cap may cause the wipers to move from a biased configuration in which the wipers extend substantially orthogonal to a longitudinal axis of the cleaning cap to a deflected configuration in which the wipers engage the distal end portion of the surgical instrument and are moved toward an inner annular wall of the cleaning cap.

In another aspect, the disclosure provides a method of cleaning a distal end portion of a surgical instrument positioned through a surgical access device. The method includes retracting a distal end portion of a surgical instrument into an instrument channel of a cleaning cap disposed over a distal portion of a surgical access device. The cleaning cap includes wipers extending radially into the instrument channel, and retraction of the surgical instrument causes the wipers to scrape clean an outer surface of the distal end portion of the surgical instrument.

The method may further include advancing the distal end portion of the surgical instrument into the instrument channel of the cleaning cap. Advancement may cause the wipers to sequentially contact a tip portion of the surgical instrument to clean the tip portion and frictionally engage the outer surface of the distal end portion to scrape clean the outer surface.

The details of one or more aspects of the disclosure are set forth in the accompanying drawings and the description below. Other features, objects, and advantages of the aspects described in this disclosure will be apparent from the description and drawings, and from the claims.

DETAILED DESCRIPTION

Figure 1:
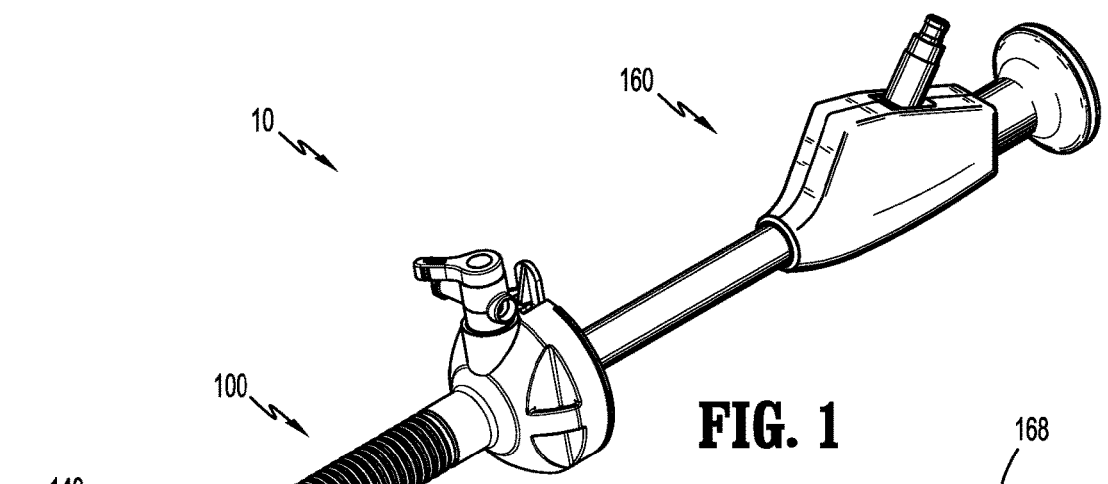
FIG. 1 is a perspective, side view of a surgical access assembly including a surgical access device, a cleaning cap, and a surgical instrument in accordance with an aspect of the disclosure.

Aspects of the present disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Surgical access assemblies with obturators, known as trocar assemblies, are employed during minimally invasive surgery, e.g., laparoscopic surgery, and provide for the sealed access of surgical instruments into an insufflated body cavity, such as the abdominal cavity. The surgical access assemblies of the present disclosure include an instrument housing mounted on a cannula. An obturator (not shown) is insertable through the instrument housing and the cannula. The obturator can have a blunt distal end, or a bladed or non-bladed penetrating distal end, and can be used to incise and/or separate tissue of the abdominal wall so that the surgical access assembly can be introduced into the abdomen. The handle of the obturator can engage or selectively lock into the instrument housing of the surgical access assembly.

Trocar assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument housing of the surgical access assembly includes valves and/or seals that prevent the escape of insufflation fluid from the body cavity, while also allowing surgical instruments to be inserted into the body cavity.

In various aspects, a bladeless optical trocar obturator may be provided that permits separation of tissue planes in a surgical procedure and visualization of body tissue fibers as they are being separated, thereby permitting a controlled traversal across a body wall. In other aspects, the trocar obturator may be bladeless without being optical, e.g., without providing contemporaneous visualization thereof through the distal tip of the trocar obturator. The bladeless trocar obturator may be provided for the blunt dissection of the abdominal lining during a surgical procedure.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905, the entire content of which is hereby incorporated by reference herein.

Figure 2:
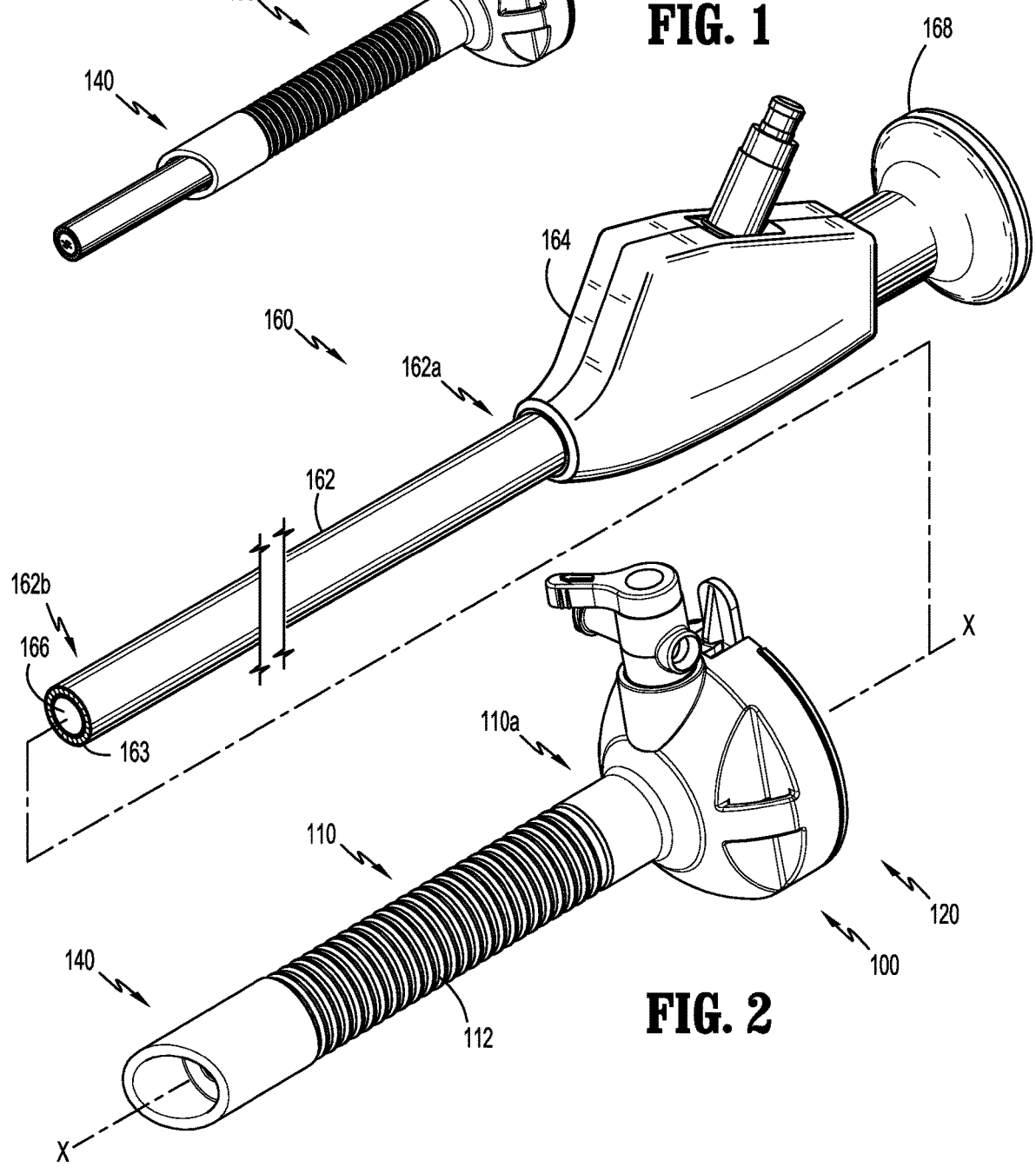
FIG. 2 is a perspective, side view of the surgical access assembly of FIG. 1, shown with the surgical instrument separated from the surgical access device.
Figure 3:
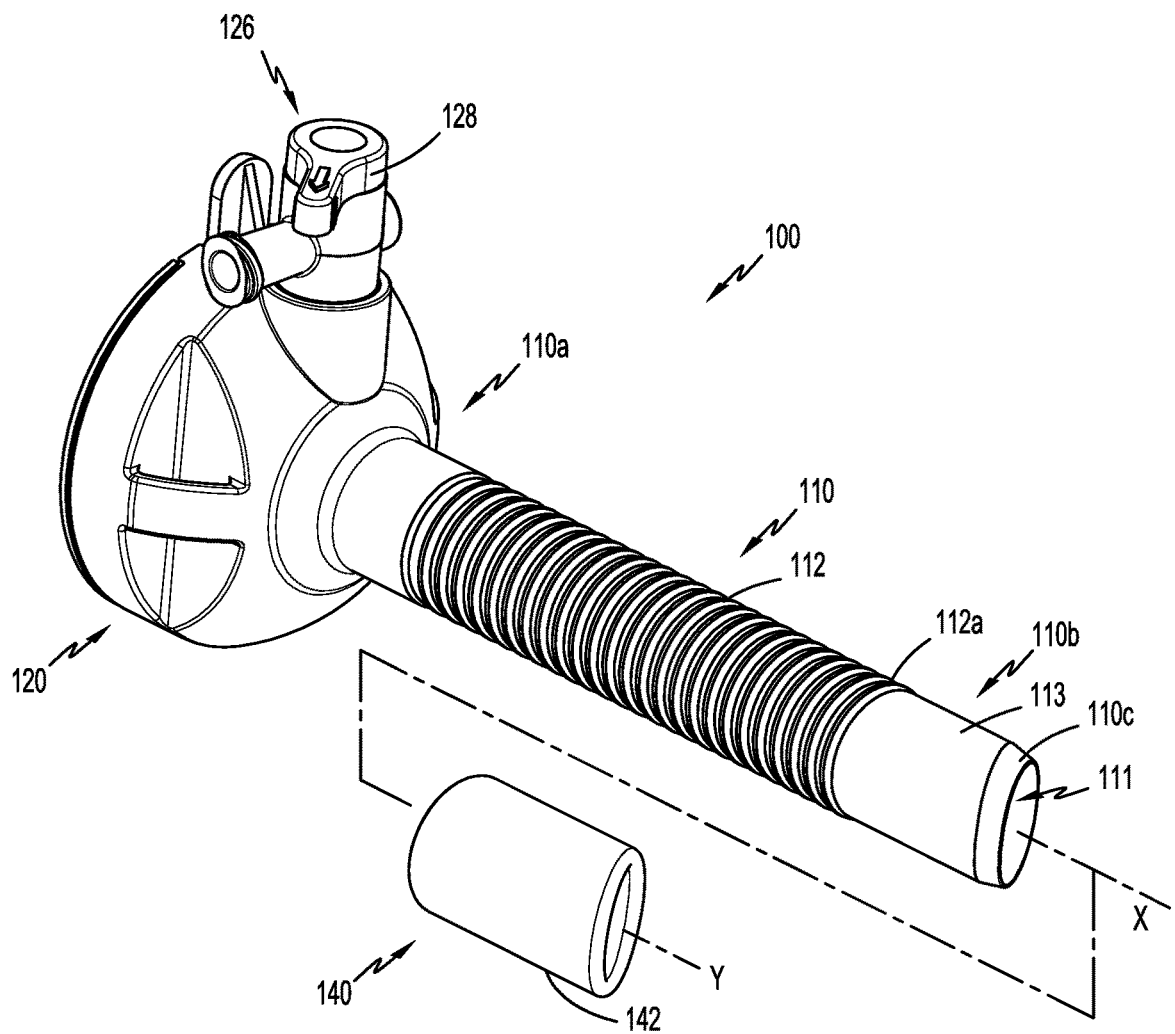
FIG. 3 is a perspective, side view of the surgical access device and the cleaning cap of the surgical access assembly of FIG. 1.
Figure 4:
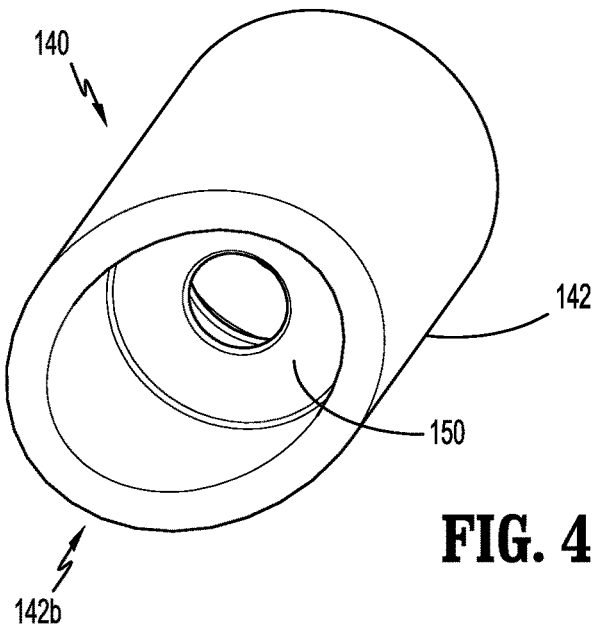
FIG. 4 is a perspective, end view of the cleaning cap of FIG. 3.
Figure 5:
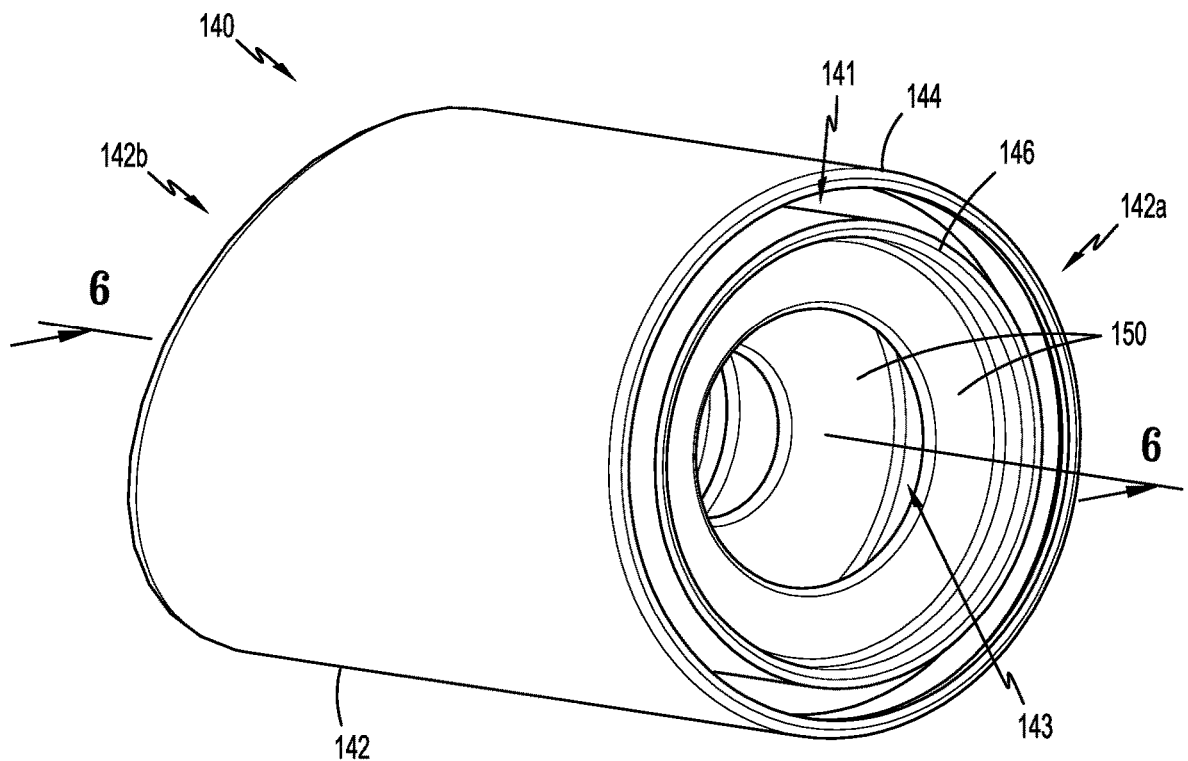
FIG. 5 is a perspective, side view of the cleaning cap of FIG. 4.
Figure 6:
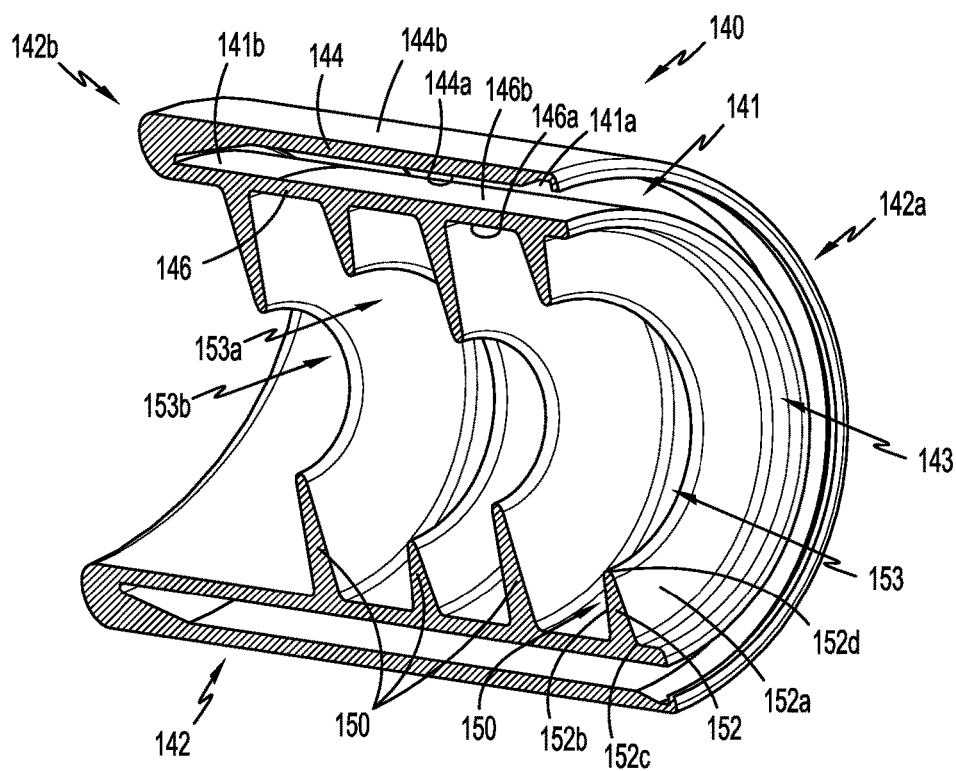
FIG. 6 is a cross-sectional view of the cleaning cap of FIG. 5, taken along section line 6-6 of FIG. 5.

FIGS. 1-3 illustrate a surgical access assembly 10 including a surgical access device 100, a cleaning cap 140 releasably engaged with the surgical access device 100, and a surgical instrument, shown as visualization device 160, positioned through the surgical access device 100. The surgical access device 100 and the visualization device 160 will further be described to the extent necessary to disclose aspects of the disclosure. For a detailed description of the structure and function of exemplary surgical access devices, reference may be made to U.S. Pat. No. 10,543,018, the entire content of which is hereby incorporated by reference herein. For a detailed description of the structure and function of exemplary visualization devices, reference may be made to U.S. Patent Appl. Pub. No. 2016/0007833, the entire content of which is hereby incorporated by reference herein. Accordingly, it should be understood that a variety of surgical access devices and visualization devices may be utilized with a cleaning cap of the present disclosure.

The visualization device 160 includes an elongated tubular body 162 having a proximal end portion 162a coupled to a handle 164 and a distal end portion 162b including a tip portion 163 containing a lens 166. The elongated tubular body 162 is adapted to conduct light therethrough and facilitate viewing through an eyepiece 168 coupled to the handle 164. Alternatively, a light source may be disposed at the distal end portion 162b (e.g., the tip portion 163) of the elongated tubular body 162 and/or the visualization device may include a camera configured to transmit video signals to an external monitor. It is envisioned that the specific structural features of the visualization device may vary so long as the device facilitates visual inspection of inner structures of a human body. The visualization device may be an endoscope, a laparoscope, or any suitable device designed for visual inspection of a body's internal structure.

The surgical access device 100 includes a cannula 110 and an instrument housing 120 secured to the cannula 110. The cannula 110 generally includes an elongated shaft 112 extending along a central longitudinal axis "X" and defining an access lumen 111 for reception and passage of a surgical instrument, such as the visualization device 160, therethrough. A proximal end portion 110a of the cannula 110 supports the instrument housing 120 thereon and a distal end portion 110b of the cannula 110 supports the cleaning cap 140.

Figure 7:
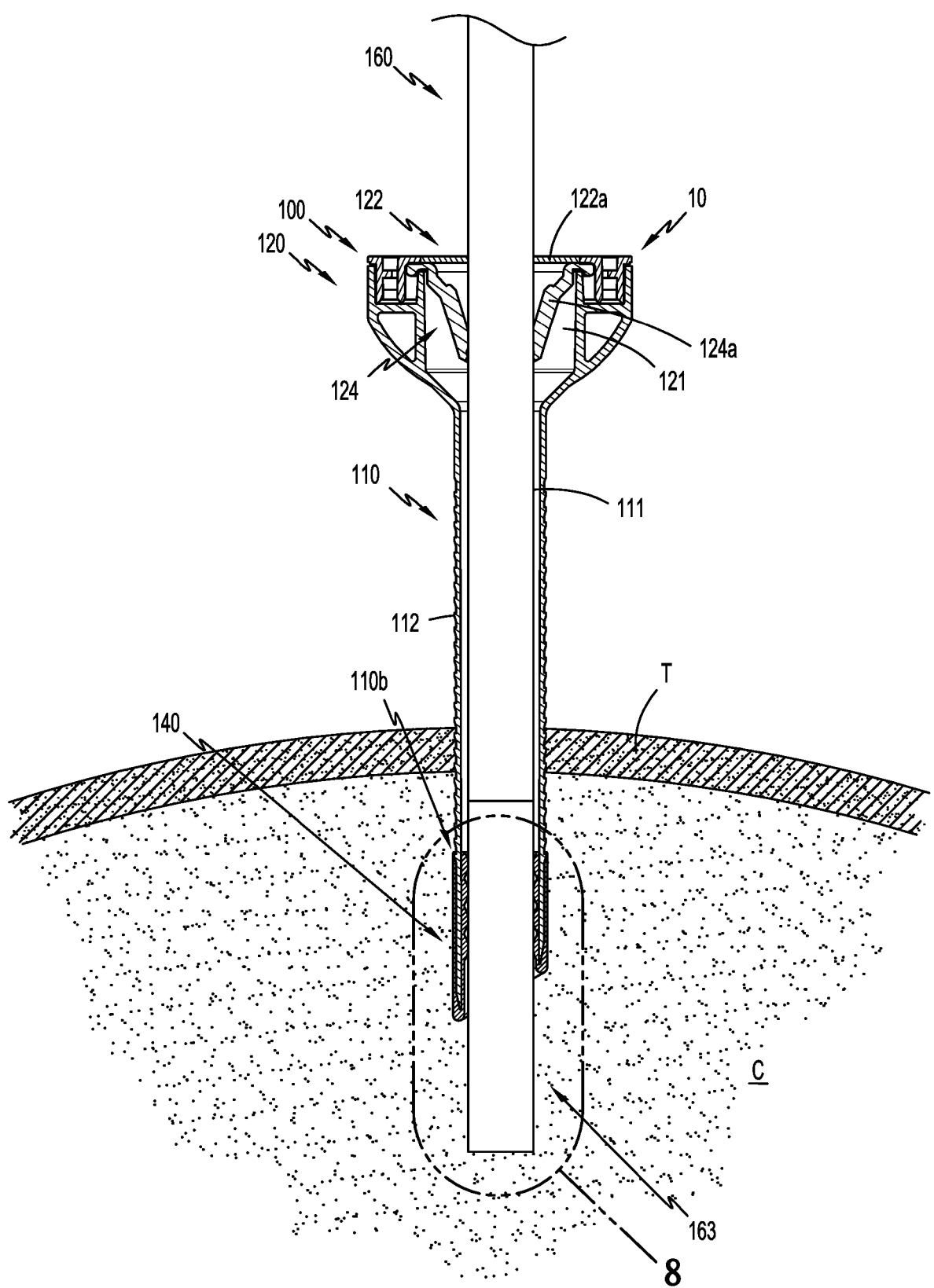
FIG. 7 is a cross-sectional view of the surgical access assembly of FIG. 1, shown positioned in tissue.

As shown in FIG. 7, the instrument housing 120 defines a cavity 121 therein that communicates with the access lumen 111 of the elongated shaft 112 of the cannula 110. The instrument housing 120 supports a seal assembly 122 and a valve assembly 124 therein. The seal assembly 122 is disposed proximally of the valve assembly 124. The seal assembly 122 generally includes an instrument seal 122a for sealing around surgical instruments (e.g., the visualization device 160) inserted into the cannula 110, and the valve assembly 124 generally includes a zero-closure seal 124a for sealing the access lumen 111 of the cannula 110 in the absence of a surgical instrument inserted through the cannula 110. The seal assembly 122 and the valve assembly 124 prevent the escape of the insufflation fluid therefrom, while allowing surgical instruments to be inserted therethrough and into the body cavity. The instrument seal 122a may include any known instrument seal used in cannulas and/or trocars, such as septum seal. The zero-closure seal 124a may be any known zero-closure seal for closing off the passageway into the access lumen 111, such as a duckbill seal or flapper valve.

With continued reference to FIG. 3, in conjunction with FIG. 7, the instrument housing 120 includes an insufflation port 126 defining an opening (not explicitly shown) therethrough that is in fluid communication with the cavity 121 of the instrument housing 120 which, in turn, is in fluid communication with the access lumen 111 of the cannula 110 to insufflate a body cavity, such as an abdominal cavity (e.g., create a pneumoperitoneum). The opening of the insufflation port 126 is disposed distally of the valve assembly 124 to maintain insufflation pressure within the body cavity. The insufflation port 126 is connectable to a source of insufflation fluid (not shown) for delivery of the insufflation fluid (e.g., gases) into the body cavity. The insufflation port 126 is configured and dimensioned to receive a valve 128 in a substantially fluid-tight manner. In aspects, and as shown, the valve 128 is a stopcock valve for controlling the flow of the insufflation fluid. The valve 128, however, may be any known valve for directing fluid flow and, in some aspects, regulating fluid flow.

With reference now to FIGS. 3-6, the cleaning cap 140 is removably positionable over the distal end portion 110b of the cannula 110 of the surgical access device 100. The cleaning cap 140 includes a body 142 extending along a longitudinal axis "Y" that is coincident with the central longitudinal axis "X" of the surgical access device 100 when the cleaning cap 140 is positioned on the surgical access device 100. The body 142 of the cleaning cap 140 includes an annular pocket 141 configured to receive the distal end portion 110b of the surgical access device 100 therein, and an instrument channel 143 configured to allow passage of a surgical instrument therethrough and to clean the surgical instrument as it passes therethrough.

The annular pocket 141 of the cleaning cap 140 is defined in an outer circumference thereof between an inner surface 144a of an outer annular wall 144 and an outer surface 146b of an inner annular wall 146 of the body 142. The annular pocket 141 is sized and shaped to frictionally engage the elongated shaft 112 of the surgical access device 100 such that the distal end portion 110b of the cannula 110 is received within the annular pocket 141 and the access lumen 111 of the cannula 110 is aligned with and in open communication with the instrument channel 143 of the body 142. In aspects and as shown, the annular pocket 141 is complementary in size and shape with the distal end portion 110b of the cannula 110 and includes a proximal cutout 141a for receiving a rib 112a of the elongated shaft 112 and a distal taper 141b for receiving the distal tip 110c of the cannula 110.

The annular pocket 141 is open at a proximal end 142a of the body 142 and is closed at a distal end 142b of the body 142. It should be understood that the body 142 may have any length and the annular pocket 141 may extend along any portion of length of the body 142. The outer annular wall 144 includes an outer surface 144b that mimics the shape of the outer surface 113 of the distal end portion 110b of the surgical access device 100. In aspects and as shown, the outer surface 144b of the cleaning cap 140 has a smooth atraumatic finish like that of the distal end portion 110b of the surgical access device 100.

The instrument channel 143 of the cleaning cap 140 is disposed radially inwardly of the annular pocket 141 and is defined by an inner surface 146a of the inner annular wall 146. The instrument channel 143 is coincident with the access lumen 111 of the surgical access device 100 when the cleaning cap 140 is positioned on the surgical access device 100 so that a surgical instrument can be passed therethrough. A plurality of wipers or fins 150 extend from the inner surface 146a of the inner annular wall 146 radially into the instrument channel 143. The wipers 150 have a biased configuration that extend substantially orthogonal to the longitudinal axis "Y." The wipers 150 are disposed in longitudinally spaced relation relative to each other along a portion or an entirety of the length of the body 142. While four wipers 150 are shown, it should be understood that the cleaning cap 140 may include more than four wipers 150 or less than four wipers 150.

Each wiper 150 has a disc-shaped body 152 including a proximal facing surface 152a, a distal facing surface 152b, an outer terminal edge 152c connected to or monolithically formed with the inner annular wall 146 of the body 142, and an inner terminal edge 152d defining an opening 153 therethrough. The opening 153 defined through each wiper 150 has a smaller dimension or diameter than that of the instrument channel 143 and is concentric with the instrument channel 143. The wipers 150 can include the same sized openings 153 or the size of the openings 153 can be different. In aspects and as shown, the wipers 150 have alternating sized openings 153a, 153b of larger and smaller sizes, respectively, that are concentric with each other along the longitudinal axis "Y" of the body 142.

The body 142 and the wipers 150 of the cleaning cap 140 are each formed from a flexible material, such as rubber, plastic, or other suitable polymer (e.g., elastomers). These materials are selected to maximize debris removal while minimizing scratching the lens 166. The body 142 and the wipers 150 may be monolithically formed from the same or common material, or the body 142 and the wipers 150 may be separate components formed from the same or different materials that are fixedly secured together. The wipers 150 have a thickness and configuration that accommodates flexing of the wipers 150 about a surgical instrument inserted therethrough during proximal and distal movement of the surgical instrument through the cleaning cap 140. In this manner, the wipers 150 clean the outer surface of the surgical instrument and limit the introduction of fluids, debris, and/or tissue into the access lumen 111 (e.g., fluids, debris, or tissue that may stick to the surgical instrument at the surgical site).

Figures 8, 9, 10:
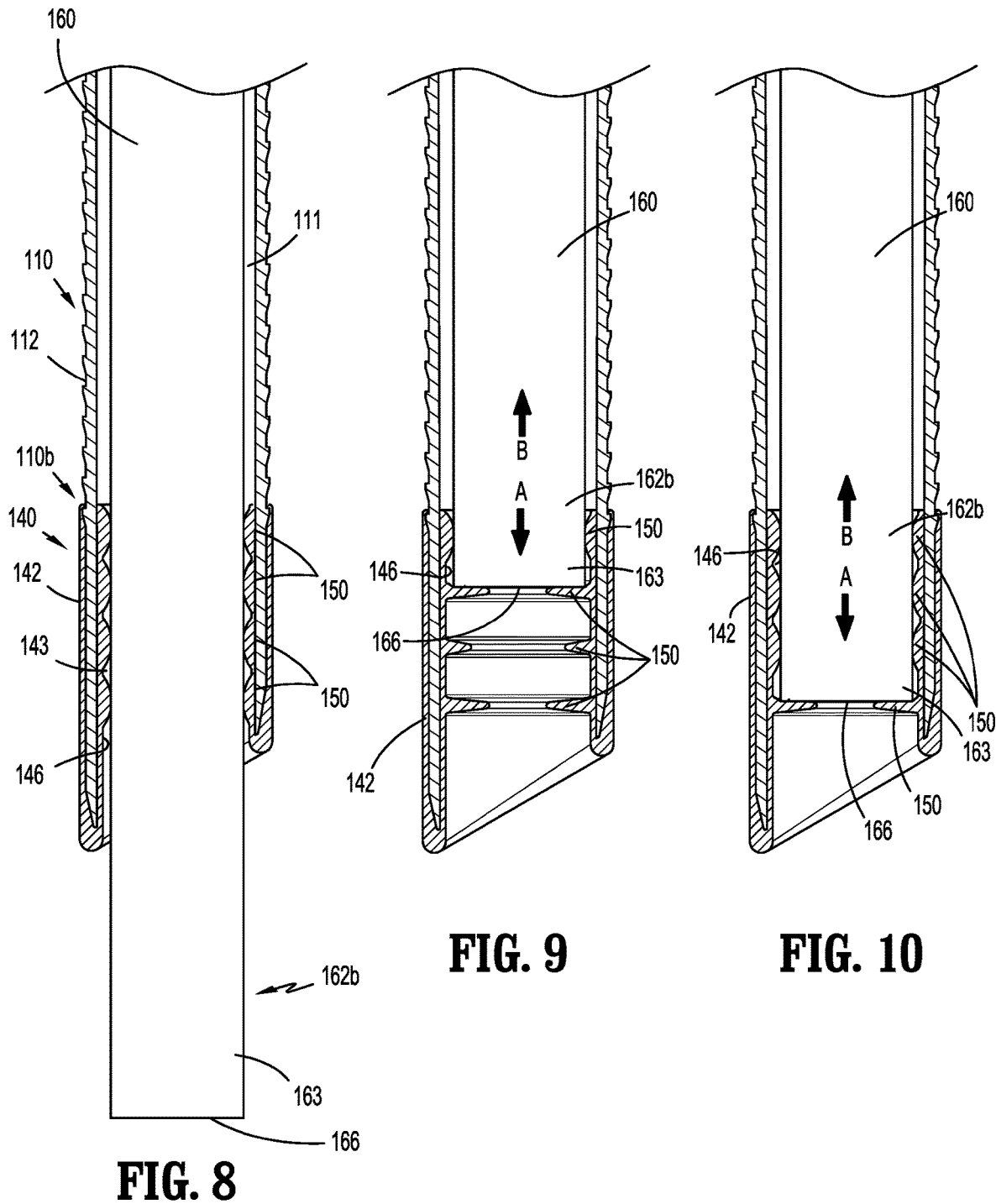
FIG. 8 is a close-up view of the area of detail indicated in FIG. 7.
FIG. 9 is a cross-sectional view of the area of detail of FIG. 8, shown with a tip portion of the surgical instrument disposed in proximal portion of the cleaning cap.
FIG. 10 is a cross-sectional view of the area of detail of FIG. 8, shown with a tip portion of the surgical instrument disposed in a distal portion of the cleaning cap.

Turning now to FIGS. 7 and 8, the cleaning cap 140 is positioned over the distal end portion 110b of the surgical access device 100 such that the instrument channel 143 of the cleaning cap 140 is disposed within and aligned with the access lumen 111 of the surgical access device 100. The surgical access device 100, with attached cleaning cap 140, may then be positioned through tissue "T," e.g., an abdominal wall. The elongated shaft 112 of the cannula 110 is received through the tissue "T" (e.g., by utilizing an obturator (not shown) to facilitate entry of the cannula 110 through the tissue "T") such that the distal end portion 110b of the surgical access device 100 and the cleaning cap 140 are positioned within a body cavity "C," such as the abdominal cavity.

The visualization device 160 is inserted through the surgical access device 100 and is advanced through the cleaning cap 140 until the tip portion 163 extends distally out of the surgical access device 100 and the cleaning cap 140, and is disposed within the body cavity "C." During advancement of the tip portion 163 of the visualization device 160 through the cleaning cap 140 (e.g., during introduction of the visualization device 160 into the body cavity "C"), in the direction of arrows "A" as seen in FIGS. 9 and 10, the distal end portion 162b of the visualization device 160 is translated distally through the wipers 150 of the cleaning cap 140 such that the tip portion 163 sequentially contacts and deflects the wipers 150 outwardly against the inner annular wall 146 of the body 142. During advancement, the outer surface of the lens 166 of the visualization device 160 contacts and is wiped clean by the wipers 150 and the outer surface of the distal end portion 162b is also wiped clean by frictional engagement of the wipers 150 therewith.

During retraction of the tip portion 163 through the cleaning cap 140 (e.g., during withdrawal of the visualization device 160 from the body cavity "C"), in the direction of arrows "B" as seen in FIGS. 9 and 10, the distal end portion 162b of the visualization device 160 is proximally translated through the wipers 150 of the cleaning cap 140. The wipers 150 maintain contact with the outer surface of the distal end portion 162b until the distal end portion 162b is moved proximally of a respective wiper 150 and the wiper 150 is free to return to its biased configuration. During retraction, the outer surface of the distal end portion 162b is wiped clean by the frictional engagement of the wipers 150 therewith, minimizing introduction of fluids, debris, and/or tissue into the surgical access device 100.

During a surgical procedure, should the lens 166 of visualization device 160 become obstructed, the visualization device 160 may be retracted and advanced through the cleaning cap 140 to scrape off fluid, debris, and/or tissue. The wipers 150 clean the visualization device 160 as it is passed through the access lumen 111 of the surgical access device 100. The wipers 150 may also create a seal around the tubular body 162 of the visualization device 160 when the visualization device 160 is disposed therethrough allowing for longitudinal movement of the visualization device 160 relative thereto while minimizing the entrance of fluid, debris, and tissue into the access lumen 111 of the surgical access device 100 (e.g., during insertion, withdrawal, and manipulation of the visualization device 160).

Figure 11:
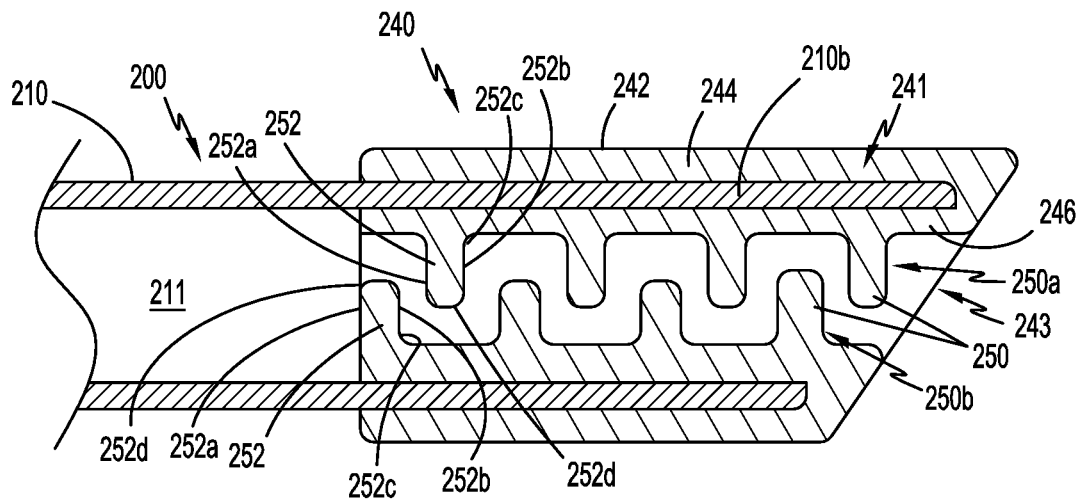
FIG. 11 is a cross-sectional view of a distal end portion of a surgical access device and a cleaning cap in accordance with another aspect of the present disclosure.
Figure 12:
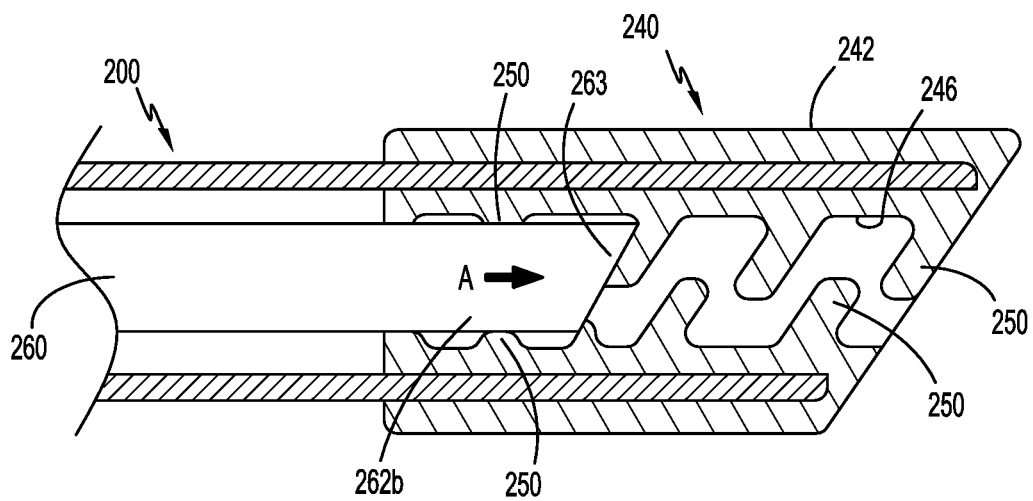
FIG. 12 is a cross-sectional view of the surgical access device and the cleaning cap of FIG. 11, shown with a surgical instrument extending therethrough.

Turning now to FIGS. 11 and 12, a cleaning cap 240 in accordance with another aspect of the disclosure is shown. The cleaning cap 240 is substantially similar to the cleaning cap 140 and will be described with respect to the differences therebetween. Accordingly, it should be understood that various components of the disclosure, such as those numbered in the 100 series, correspond to components of the disclosure similarly numbered in the 200 series, such that redundant explanation of similar components need not be repeated herein.

The cleaning cap 240 includes a body 242 having an annular pocket 241 defined between outer and inner annular walls 244, 246 of the body 242 that is configured to receive the distal end portion 210b of a cannula 210 of a surgical access device 200 therein, and an instrument channel 243 defined within the inner annular wall 246 of the body 242 that is configured to allow passage of a surgical instrument therethrough and to clean the surgical instrument as it passes therethrough.

A plurality of wipers or fins 250 extend from the inner annular wall 246 radially into the instrument channel 243. The wipers 250 include a first set 250a extending from a first side of the inner annular wall 246 and a second set 250b extending from a second side of the inner annular wall 246. Each wiper 250 has a semicircular or half-disc shaped body 252 including a proximal facing surface 252a, a distal facing surface 252b, an outer terminal edge 252c connected to or monolithically formed with the inner annular wall 246 of the body 242, and an inner terminal edge 252d. The first and second sets 250a, 250b of wipers 250 are disposed in opposed relation relative to each other and are longitudinally offset with respect to each other.

Together, the first and second sets 250a, 250b of wipers 250 define a tortuous or undulating path through the instrument channel 243 of the cleaning cap 240. The wipers 250 can be extend the same distance into the instrument channel 243, or the radial length of the wipers 250 may vary. It should be understood that each wiper 250 may have any suitable shape and/or size, and that the configuration of the first and second sets 250a, 250b of wipers 250 may vary so long as the tortuous or undulating path is maintained through the instrument channel 243.

The cleaning cap 240 is positioned over the distal end portion 210b of the surgical access device 200 such that the instrument channel 243 of the cleaning cap 240 is disposed within and aligned with the access lumen 211 of the surgical access device 200. As shown in FIG. 12, a surgical instrument 260 is inserted through the surgical access device 200 and is advanced through the cleaning cap 240 in the direction of arrow "A." During advancement, the tip portion 263 of the surgical instrument 260 sequentially contacts and deflects the wipers 250 outwardly against the inner annular wall 246 of the body 242, thus cleaning the distal end portion 262b of the surgical instrument 260. During retraction of the tip portion 263 of the surgical instrument 260, in a direction opposite arrow "A," the wipers 250 maintain contact with the distal end portion 262b of the surgical device 260 thus, cleaning the distal end portion 262b of the surgical instrument 260 and minimizing the introduction of fluids, debris, and/or tissue into the surgical access device 200. Further, during use of the surgical instrument 260, should the distal end portion 262b of the surgical instrument 260 need to be cleaned, the distal end portion 262b may be advanced and retracted within the cleaning cap 240 (e.g., in a back and forth motion) to clean the distal end portion 262b of any obstructions.

While the cleaning cap is described for use with a visualization device, it should be understood that the cleaning cap may be utilized with other surgical instruments introduced through a surgical access device to clean the distal end portions thereof. It should be further understood that the cleaning cap is suitable for use with any surgical access device (e.g., rigid sleeve) through which a surgical instrument is passed.

Further, in addition to being formed from a flexible material, the one or more of the wipers or portions thereof (e.g., the proximal facing surface and/or the inner terminal edge) may include additional layers (e.g., a pad, sponge, or swab) and/or cleaning solutions to facilitate cleaning of a distal end portion of a surgical instrument passed therethrough (e.g., the lens of a visualization device).

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects may be combined with the elements and features of certain other aspects without departing from the scope of the disclosure, and that such modifications and variation are also included within the scope of the disclosure. For example, it is envisioned that a cleaning cap of the present disclosure may include a combination of wipers (e.g., wipers 250 may be provided between wipers 150 within a single cleaning cap). Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical access assembly comprising:
   a surgical access device including an elongated shaft and an access lumen defined through the elongated shaft, the elongated shaft including an outer surface having at least one rib and a distal portion terminating at a distal tip; and
   a cleaning cap including an inner annular wall, an outer annular wall, and an annular pocket defined between the inner annular wall and the outer annular wall, an opening into the annular pocket being defined at a proximal end of the cleaning cap between a proximal end of the inner annular wall and a proximal end of the outer annular wall, the annular pocket configured to receive the distal portion of the elongated shaft, the annular pocket including a cutout defined in an inner surface of the outer annular wall that is configured to receive the at least one rib of the elongated shaft, the cleaning cap including an instrument channel defined by an inner surface of the inner annular wall, the instrument channel aligned with the access lumen, the cleaning cap including wipers disposed within the instrument channel.

2. The surgical access assembly of claim 1, wherein the instrument channel is disposed within the access lumen of the surgical access device.

3. The surgical access assembly of claim 2, wherein the wipers extend from the inner surface of the inner annular wall radially into the instrument channel.

4. The surgical access assembly of claim 1, wherein the cleaning cap mimics the shape of the distal portion of the surgical access device, the distal tip of the surgical access device is angled relative to a longitudinal axis of the elongated shaft and a distal end of the cleaning cap is angled relative to a longitudinal axis of the cleaning cap.

5. The surgical access assembly of claim 1, wherein the wipers are formed from a flexible material.

6. The surgical access assembly of claim 5, wherein the wipers are formed from rubber.

7. The surgical access assembly of claim 5, wherein the cleaning cap is monolithically formed from the flexible material and the wipers extend from the inner annular wall into the instrument channel.

8. The surgical access assembly of claim 1, wherein each of the wipers includes a full disc-shaped body defining an opening through the wiper that has a smaller diameter than that of the instrument channel.

9. The surgical access assembly of claim 8, wherein the wipers are disposed in longitudinally spaced relation relative to each other.

10. The surgical access assembly of claim 9, wherein the openings of the wipers vary in size and are concentric with each other.

11. The surgical access assembly of claim 2, wherein each of the wipers includes a partial disc-shaped body.

12. The surgical access assembly of claim 11, wherein a first set of the wipers extends from a first side of the inner surface of the inner annular wall radially into the instrument channel and a second set of the wipers extends from a second side of the inner surface of the inner annular wall radially into the instrument channel.

13. The surgical access assembly of claim 12, wherein the first and second sets of the wipers are disposed in opposed relation relative to each other and are longitudinally offset with respect to each other to define a tortuous path through the instrument channel.

14. The surgical access assembly of claim 1, further including a surgical instrument including an elongated tubular body having a distal end portion terminating at a tip portion, the elongated tubular body of the surgical instrument positionable through the surgical access device and the cleaning cap.

15. The surgical access assembly of claim 14, wherein the surgical instrument is a visualization device including a lens disposed at the tip portion.

16. The surgical access assembly of claim 14, wherein the distal end portion of the surgical instrument is movable through the cleaning cap in proximal and distal directions and wherein movement of the surgical instrument within the cleaning cap causes the wipers to move from a biased configuration in which the wipers extend substantially orthogonal to a longitudinal axis of the cleaning cap to a deflected configuration in which the wipers engage the distal end portion of the surgical instrument and are moved toward an inner annular wall of the cleaning cap.

17. The surgical access assembly of claim 1, wherein a distal portion of the annular pocket tapers distally and is configured to receive the distal tip of the surgical access device.

18. The surgical access assembly of claim 1, wherein the proximal end of the inner annular wall is diametric to the proximal end of the outer annular wall.

19. A method of cleaning a distal end portion of a surgical instrument positioned through a surgical access device, the method comprising:
   retracting a distal end portion of a surgical instrument into an instrument channel of a cleaning cap that is coupled to a surgical access device, the cleaning cap including an annular pocket having a cutout, an opening into the annular pocket being defined at a proximal end of the cleaning cap between a proximal end of an inner annular wall and a proximal end of an outer annular wall, a distal portion of the surgical access device being disposed within the annular pocket and a rib of the surgical access device being disposed within the cutout, the cleaning cap including wipers extending radially into the instrument channel, wherein retraction of the surgical instrument causes the wipers to scrape clean an outer surface of the distal end portion of the surgical instrument.

20. The method according to claim 19, further including:
   advancing the distal end portion of the surgical instrument into the instrument channel of the cleaning cap, wherein advancement causes the wipers to sequentially contact a tip portion of the surgical instrument to clean the tip portion and frictionally engage the outer surface of the distal end portion to scrape clean the outer surface.

* * * * *